(12) United States Patent
Vilkomerson

(10) Patent No.: US 6,176,829 B1
(45) Date of Patent: Jan. 23, 2001

(54) MULTI-BEAM DIFFRACTION GRATING IMAGER APPARATUS AND METHOD

(75) Inventor: David Vilkomerson, Princeton, NJ (US)

(73) Assignee: Echocath, Inc., Princeton, NJ (US)

( * ) Notice: Under 35 U.S.C. 154(b), the term of this patent shall be extended for 0 days.

(21) Appl. No.: 09/256,633

(22) Filed: Feb. 24, 1999

Related U.S. Application Data

(60) Provisional application No. 60/076,037, filed on Feb. 26, 1998.

(51) Int. Cl.[7] .................................................. A61B 8/00
(52) U.S. Cl. ........................................ 600/443; 600/459
(58) Field of Search .................................. 600/437, 443, 600/447, 459; 73/644

(56) References Cited

U.S. PATENT DOCUMENTS

| | | | | |
|---|---|---|---|---|
| 4,350,917 | * | 9/1982 | Lizzi et al. .......................... | 310/320 |
| 4,485,321 | * | 11/1984 | Klickey et al. ..................... | 310/322 |
| 4,549,533 | * | 10/1985 | Cain et al. .......................... | 600/447 |
| 4,561,019 | * | 12/1985 | Lizzi et al. .......................... | 358/112 |
| 5,113,706 | * | 5/1992 | Pittaro ................................. | 600/447 |
| 5,360,007 | * | 11/1994 | Shinomura et al. ................. | 600/447 |
| 5,373,845 | * | 12/1994 | Gardineer et al. .................. | 600/445 |
| 5,696,737 | * | 12/1997 | Hossack et al. ..................... | 367/138 |
| 5,713,362 | * | 2/1998 | Vilkomerson ....................... | 600/459 |
| 5,916,210 | * | 6/1999 | Winston .............................. | 600/439 |

* cited by examiner

*Primary Examiner*—Francis J. Jaworski
(74) *Attorney, Agent, or Firm*—Arthur L. Plevy; Buchanan Ingersoll PC

(57) ABSTRACT

An ultrasonic imaging apparatus comprising a transducer operative for receiving a pulse of energy containing multiple frequencies and generating a plurality of beams at different angles corresponding to a plurality of frequencies toward an object to be imaged; means for focusing said beams to produce an array of focused points at spatial positions on the object; a receiver for receiving reflected signals from the object having frequencies corresponding to the spatial positions and simultaneously filtering the reflected signals to produce sample image data sets corresponding to spatial positions at particular time intervals; and means for producing rotational motion between the transducer and the object to enable generation of sample image data sets at other predetermined spatial positions; and means for summing the sample image data sets at each of the predetermined spatial positions to produce an image of the object.

8 Claims, 7 Drawing Sheets

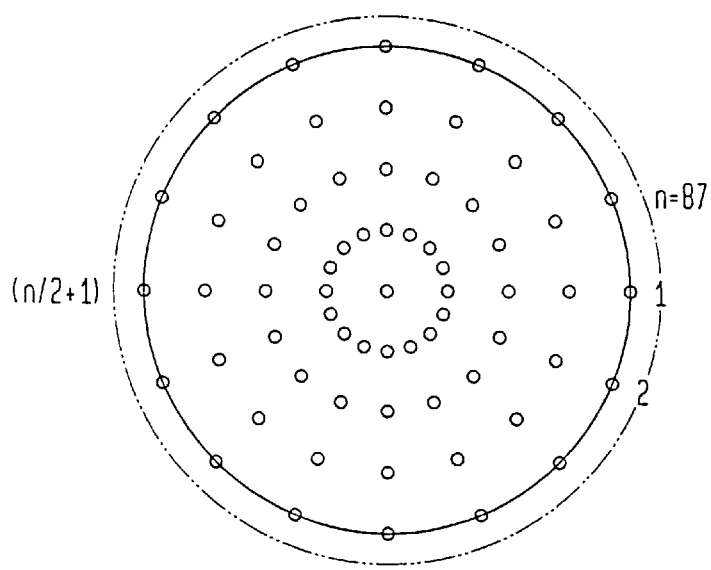
FIG. 7
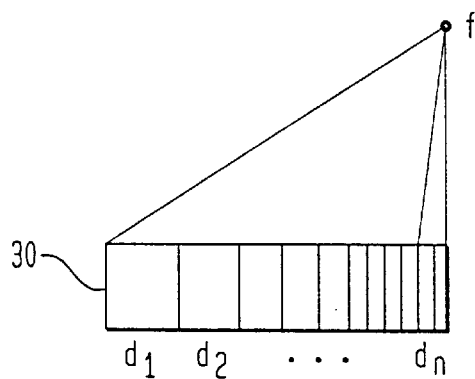
FIG. 8
FIG. 9
(PRIOR ART)
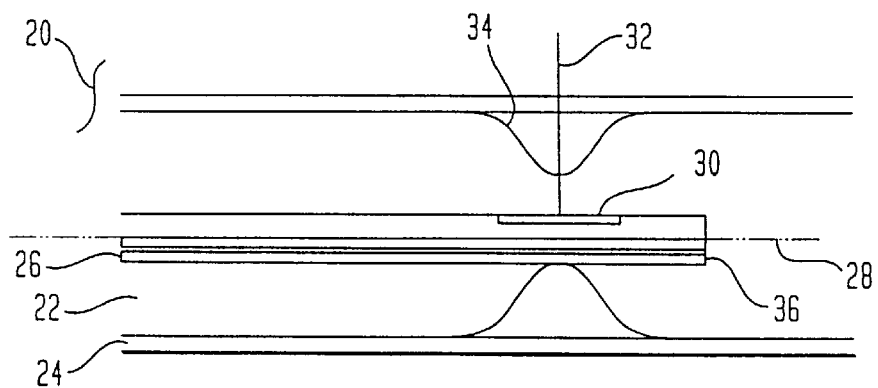

MULTI-BEAM DIFFRACTION GRATING IMAGER APPARATUS AND METHOD

RELATED APPLICATIONS

This application is related to co-pending provisional patent application Ser. No. 60/076,037 filed on Feb. 26, 1998 entitled MULTI-BEAM DIFFRACTION GRATING IMAGER APPARATUS AND METHOD.

FIELD OF THE INVENTION

The present invention relates to imaging systems, and more particularly, to imaging systems employing focus means and rotating quadrature-diffracting transducers using multiple frequencies for generating a three dimensional view of an object from the parallel collection of image data.

BACKGROUND OF THE INVENTION

There exists in medicine an important and continuing need to quickly and accurately image both blood and tissue in order to facilitate proper diagnosis and treatment of various medical conditions. A prior art technique of providing an image of a lumen employs X-ray fluoroscopy. In X-ray fluoroscopy, a contrast agent is sent through an artery of interest. The contrast agent is visible under X-ray radiation which enables an X-ray system to provide an image of the arterial obstruction. However, such X-ray imaging techniques have disadvantages. An X-ray image of an arterial obstruction is a profile of the contrast agent as it flows through the artery. Therefore, the images provided are generally of the contrast agent in a single plane of view, not of the tissue. Moreover, the true lumen diameter is generally not provided by these images. In addition, the characteristics of the plaque within the artery are not provided, which is important in determining the success of a possible angioplasty procedure. Another disadvantage is the potential harmful effects of the radiation to the patient and attending medical personnel. Furthermore, there is potential for additional harmful effects due to the contrast agent.

In prior art ultrasound imaging systems, a transducer is utilized that emits an ultrasonic imaging beam. The transducer may be fastened, for example, about the outside circumference of a catheter and the ultrasonic imaging beam emanates perpendicular to the catheter. Because of this, the transducer only provides an image of areas on the sides of the catheter, as shown in FIG. 9. Such prior art catheter side scanning systems generally do not provide an image of the central region of the lumen in front of the catheter tip. This is a disadvantage since it is the central region of the lumen that should be imaged in order to characterize a severe stenosis. These systems can produce volumetric images by moving the catheters along the vessel, storing the 2D images, and then constructing a volumetric image, but not in real-time and only in a cylindrical volume around the path of the catheter.

In addition, such prior art side scanning systems proceed blindly forward through the blood vessel as the catheter is moved. This forward, unchecked motion may inadvertently cause the catheter to contact the blood vessel wall and shear off material attached to the blood vessel wall so that it is pushed into the bloodstream. Furthermore, such prior art side scanning systems generally do not provide for the guidance of therapeutic procedures such as laser ablation or mechanical atherectomy. Moreover, prior art catheter side scanning systems provide a plane image on the side of the catheter, which prevents a substantial portion of many pathologies from being characterized.

Another prior art technique utilizes a catheter that is volume imaging and front looking but does not employ ultrasonic imaging techniques. U.S. Pat. No. 4,998,916 to Hammerslag, et al discloses a steerable catheter device for coronary angioplasty applications. The device can negotiate the tortuous character of a vascular system. Fiber optic bundles are located at the tip of the device that illuminate an area in front of the device. In order to visualize a volume, a transparent inert liquid, such as a saline solution, must be discharged into the vascular system. The transparent liquid is discharged in front of the device and displaces blood from the front of the device. This enables a user to view through the liquid and observe the volume in front of the device.

However, systems employing fiber optics have disadvantages. One disadvantage is that essentially only the surfaces of the pathologies can be seen. In addition, the liquid utilized must be replaced frequently since it will dissipate and is absorbed into the vascular system. Therefore, the amount of time that this prior art device can be used is dependent upon the ability of the patient's vascular system to absorb the liquid. Moreover, this technique is not particularly reliable and is time consuming to use and therefore relatively expensive.

Still another technique is to use a transducer nutatably mounted on the tip of a probe for luminal scanning of an oncoming area or volume as the probe moves to a selected position in a lumen or body cavity. Such a front mounted transducer provides a scanning system that is forward looking and that uses ultrasound for intraluminal imaging. U.S. Pat. No. 5,373,845, entitled "Apparatus And Method For Forward Looking Volume Imaging", issued Dec. 20, 1994, to Gardineer et al., and incorporated herein by reference, discloses such a scanning system. In this patent, the beam is produced by a nutating single element transducer operating in a pulse mode and centered at a single frequency and obtains imaging data one ray at a time. Such an imaging method, however, results in an undesirably slow process. For example, use of the single element transducer for a 10 centimeter depth of field and 2,000 pixels per image would require 0.33 second per volume, which is not useful for real time visualization. Prior art does suggest using a wide angular spectrum of illumination to image. While the prior art, which includes the area of acoustical holography, suggests using grating-like structures to form multiple illuminating beams, the prior art fails to provide a useful and rapid image formation mechanism by which to generate full 3-D volume images. Thus, it is greatly desirable to increase the speed at which the image is formed in order to provide a more useful ultrasound imaging system.

Three-dimensional realtime ultrasound imaging systems have been devised. In particular, real-time ultrasound volumetric imaging has been performed by using multiple beams at a time. Von Ramm et al. U.S. Pat. No. 4,694,434, teaches the use of a 2-dimensional phased array with the transmission of a single beam and multiple "receive beams" for multiple transmit beams and one or more receive beams) to acquire the data required for 3D reconstruction in real time. This apparatus requires a 2-dimensional phased array structure, as well as phase-controllable receive channels on each element of the array. Such a system is expensive, and the number of cables required for the 2D phased array would preclude use in an internal, catheter-based imaging system.

U.S. Pat. No. 5,720,708 entitled HIGH FRAME RATE IMAGING WITH LIMITED DIFFRACTION BEAMS discloses the use of multiple simultaneous beams from a single pulse and decodes the echoes from the multiple beam so as to obtain multiple imaging points. In similar fashion to U.S.

Pat. No. 4,694,434, this patent also requires a two-dimensional array where each individual element in the two-dimensional array must be connected to individual channels requiring a plurality of cables and complex interconnections. The decoding of the signal containing the multiple beam reflections also requires complicated mathematical processing involving two-dimensional Fourier transforming. Moreover, the field of view is limited to approximately the size of the array, thereby limiting the use for invasive internal body imaging. Accordingly, an apparatus and process for generating full 3-D volume images in a rapid and efficient manner which minimizes the cable interconnections, as well as simplifying the signal processing and filtering and which allows examination of a volume or object which is much larger than the imaging system itself, is greatly desired.

BRIEF DESCRIPTION OF THE DRAWINGS

The invention is to be explained in more detail below based on embodiments depicted in the following figures where:

FIG. 7 is a diagram of a complete scan consisting of a series of line images as shown in FIG. 5, formed by rotating the apparatus by a small angle between pulses according to the present invention.

FIG. 8 is a diagram showing the unequal spacing of elements of a transducer to provide an alternative embodiment of the present invention.

FIG. 9 shows a prior art ultrasonic side scanning system.

DETAILED DESCRIPTION OF THE INVENTION

Before embarking on a detailed discussion, the following should be understood. The basic idea of the present invention, in contrast to the prior art, and in particular, to U.S. Pat. No. 5,373,845 or 4,694,434 is the use of ultrasound energy in the form of multiple simultaneous beams generated from a diffracting grating (preferably a quadrature diffraction grating) to form a volume image of a body using the backscattered energy. The present invention uses the fact that the diffracting grating transducer converts a given driving frequency into a beam at an angle given by $\theta = \sin^{-1}(\lambda/d)$, where $\lambda$ is the wavelength of the frequency and d is the spacing of the grating. Because the diffraction grating transducer is a linear system, if the diffraction grating is driven by multiple frequencies it will produce multiple beams corresponding to the multiple frequencies (for example, an optical diffraction grating thus produces a rainbow of colors from white light). Accordingly, the present invention produces a broad swath of ultrasound, with high frequency (small $\lambda$) beams at low angles and low frequency (large $\lambda$) beams at high angles to the transducer structure. As different frequencies produce differently angled beams, the echoes from each of the beams can be separated from the rest by frequency filters, so that, in effect, a number of pulse-echo ultrasound imaging beams may be processed in parallel, thus increasing the rate at which one can form images. This leads to the formation of real-time 3D images that would otherwise be impossible to form using conventional imaging techniques. The increase in speed of image formation thus represents a major advantage of this technique.

Figure 4:
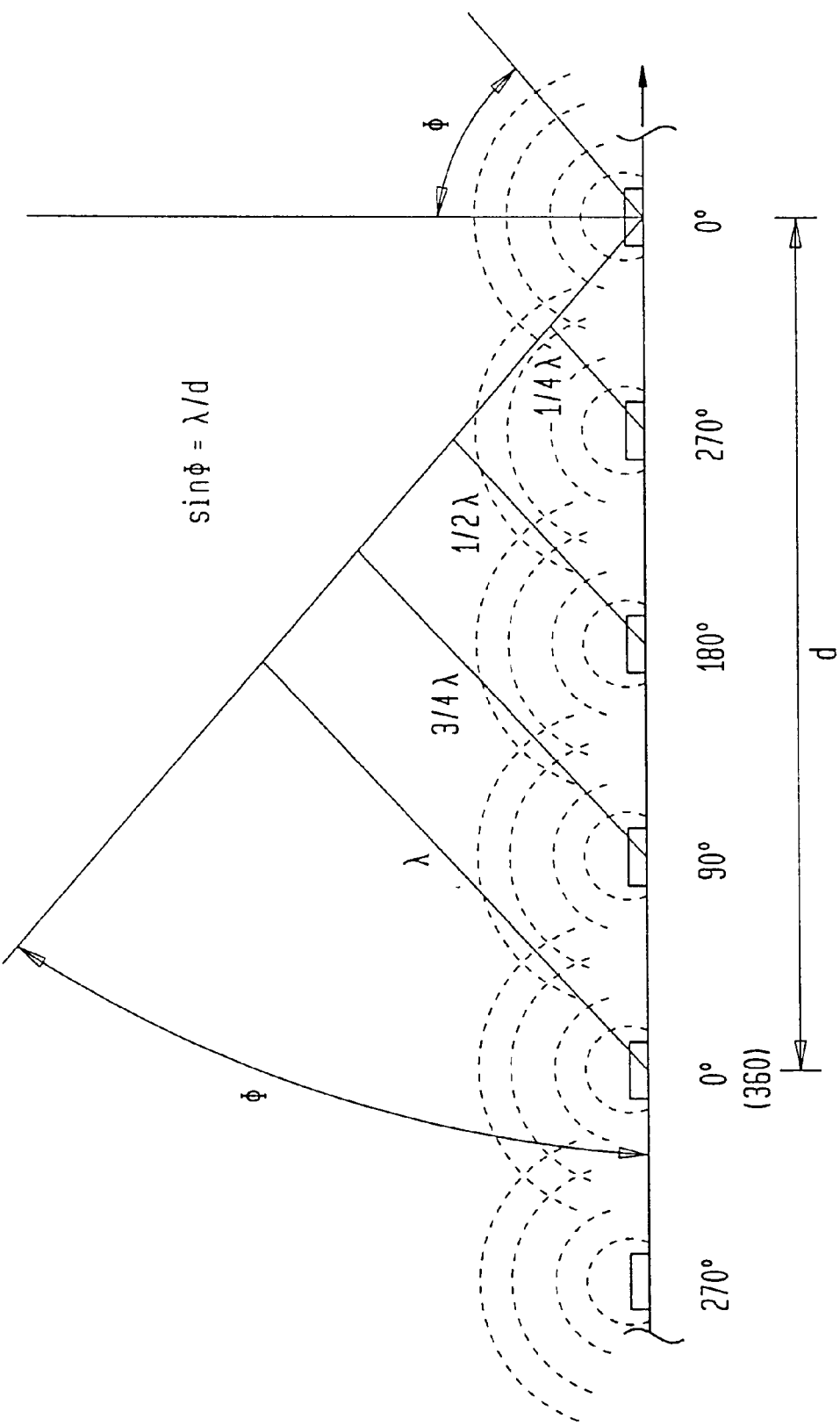
FIG. 4 is a diagram of a prior art Doppler Diffraction Grating Transducer employed in the present invention.

In accordance with the present invention, a focusing means, e.g. a lens, is used to physically separate different angle beams produced by a diffraction grating. In particular, the diffraction grating preferably used is a quadrature diffraction grating transducer where each transducer element is ninety degrees out of phase with another, as previously described for Doppler use in U.S. Pat. Nos. 5,488,953 and 5,540,230, the structure and function of which is incorporated herein by reference. FIG. 4 shows a diagram of a diffraction grating transducer (DGT) 10 which includes a grating-like structure 11 comprising an array of line transducer elements 12 each separated from one another by a distance d/4 and excited by a pulse generator 13. As shown, the DGT produces a beam at an angle given by $\phi = \arcsin(\lambda/d)$ where $\lambda$ is the wavelength of the ultrasound and d is the periodicity. As one can ascertain, changing the frequency of excitation of the transducer changes the ratio of $\lambda$ to d, and thus changes the beam angles.

Figure 1A:
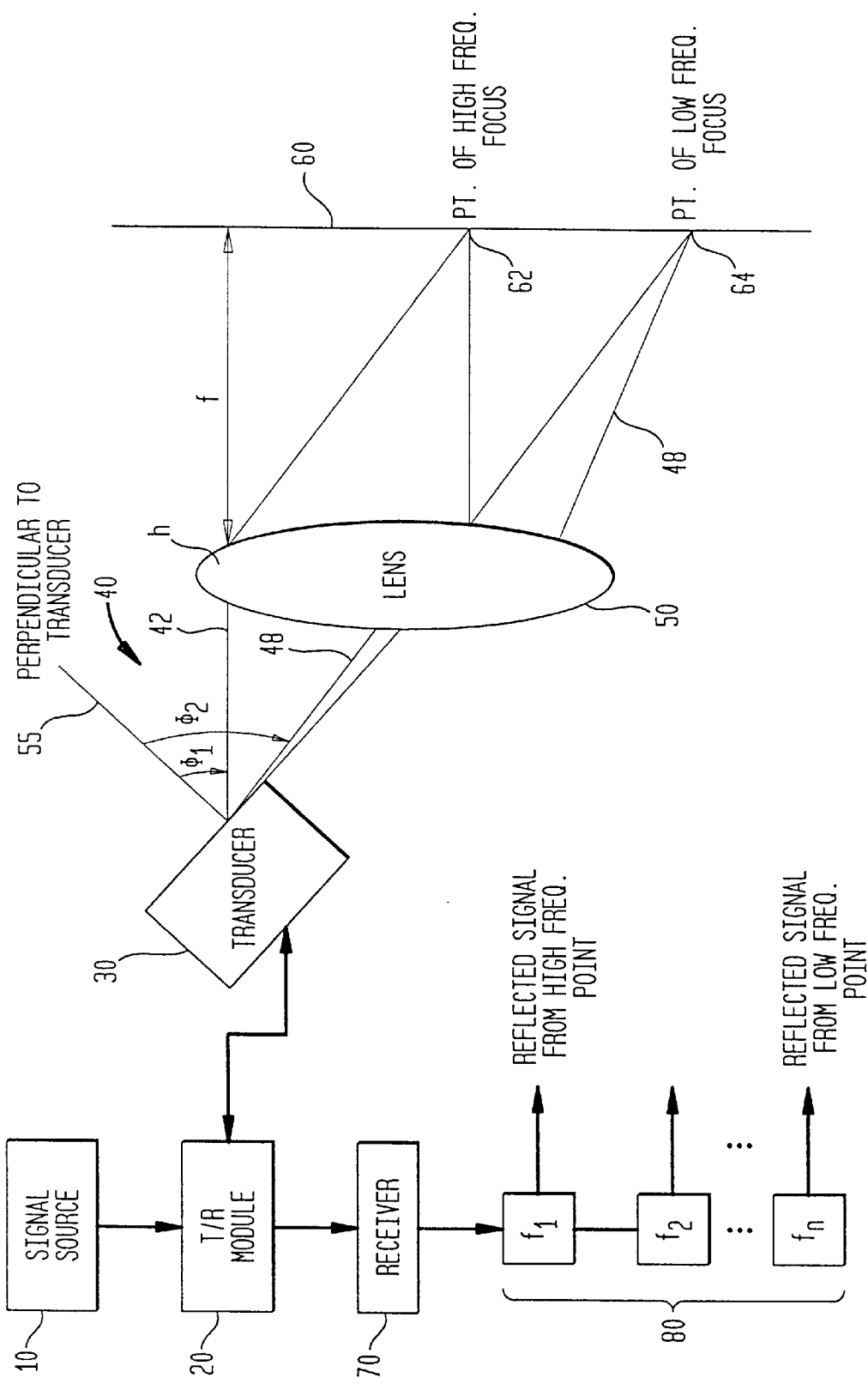
FIG. 1A is a diagram of the imaging system apparatus according to the present invention.

In the present invention, the concept is to separate different angle beams produced by the DGT by using a focussing means such as a lens. Such concept uses the relation between the angle of a parallel beam impinging on a lens and the point in the focal plane to which that beam focuses, that point being that which a ray in the bundle making up the beam passes through the middle of the lens, strikes the focal plane (as is done in ray-tracing). This is shown in FIG. 1A. By selecting a focusing means, one achieves two advantages over prior art systems: the volume insonofied is determined by the characteristics of the DGT, lens, and frequency range used, and each point in the focal plane is illuminated by a range of ray-angles thereby insuring that some backscattered energy will reach the transducer (similar to the way a condenser lens improves the illumination in a microscope). Through this method, improved imaging results.

Referring now to FIG. 1A, there is shown an imaging system according to the present invention. The imaging system comprises a signal generator 10 for generating a short time duration signal, i.e. a wide-band signal, into transmit receive module (TR module 20). The signal generator or pulse generator 10 produces a series of such pulses of such short time interval pulses at a predetermined pulse rate. The transmit receive module 20 coupled to the pulse generator 10 transmits each of the pulses to diffraction grating transducer 30. The diffraction grating transducer 30 thus produces multiple beams corresponding to multiple frequencies 40 ranging from a high frequency generated at a given angle $\phi 1$ from transducer 30 to a low frequency at an angle $\phi 2$ from the transducer. As shown in FIG. 1A, the angles are measured from a plane perpendicular to the transducer (55). Each of the multiple beams and hence multiple frequencies in the spectral domain, which result from the impulse generated by the pulse generator, impinge at different angles onto lens 50. (As the single pulses contains a continuum of frequencies, the actual distribution of acoustic energy will be continuous, like a blur, we will for convenience refer to individual beams making up the image formation, as after filtering each frequency range can be considered a "beam".) Focusing lens 50 receives the multiple frequency beams and focuses the different frequency signals to a series of intensity points or spots on the back focal plane 60. In the preferred embodiment, lens 50 is an acoustic lens made of plastic, such as polystyrene or other suitable material with an acoustic refractive index relative to tissue different from 1. (Polystyrene, for example, has an index of refraction versus water of approximately 0.66.) As the refractive index is less than 1, a plastic lens needs to be concave, as opposed to a glass lens which must be convex to focus the spots onto the focal plane. While the drawings show the lenses as convex, such a schematic representation is illustrative of how the system works and the usual convention for showing a lens is as a convex structure. In the actual embodiment, the lens will be a concave surface, rather than the convex lens shown as the schematic representation of the lens function depicted in FIGS. 1A and 1B.

Figure 5:
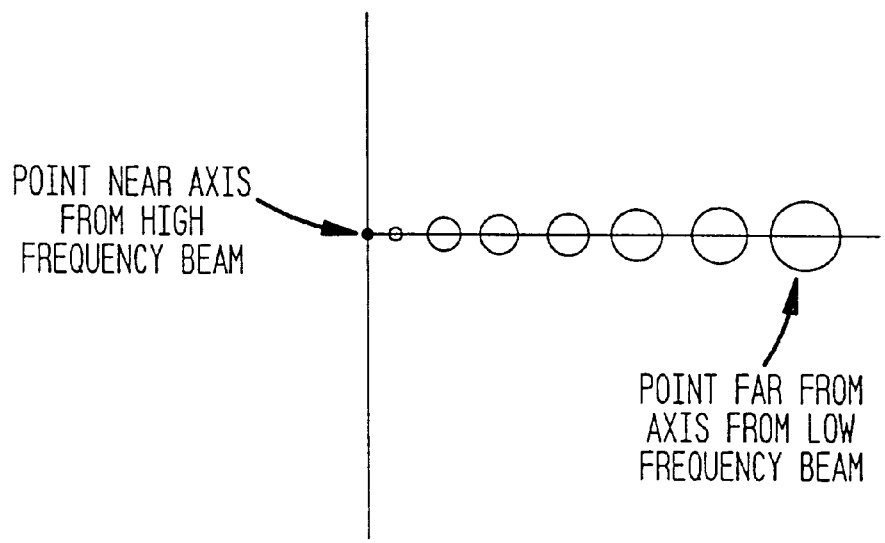
FIG. 5 is a diagram of a line of an image consisting of a series of points resulting from a single pulse from a signal source according to the present invention.

The position of the spots on the focal plane correspond to the frequency (i.e., angle) values associated with each of the beams. Each of the focus spots, as is well known through the use of conventional ray tracing, produce reflected signals which travel back through the focussing lens 50 to the quadrature diffraction grating transducer 30 which delivers the reflected signals to receiver 70. (The transmit-receive module now blocks the signal energy from going to the signal source 10.) The reflected signals of all the frequencies sent to the receiver 70 is input to a bank of filters 80, each filter being tuned to a distinct frequency range in order to capture that back scattered frequency associated with the reflected energy from one portion of the focal plane. Because the back scattered frequency signals can be captured simultaneously using the bank of filters, a line image of the object at the focal plane is generated, as shown in FIG. 5. By rotating the transducer module 30 and lens 50 at pre-defined angles about its axis in obtaining the reflected signals, a series of lines of points (i.e. like spokes in a wheel) is generated, as shown in FIG. 7. By summing the magnitudes of the back scattered frequencies received over the course of the rotation, a three dimensional visualization of the object is formed. In the preferred embodiment, the pre-defined angles correspond to angular increments of 5° in order for providing both sufficient resolution and minimal processing time.

Figure 1B:
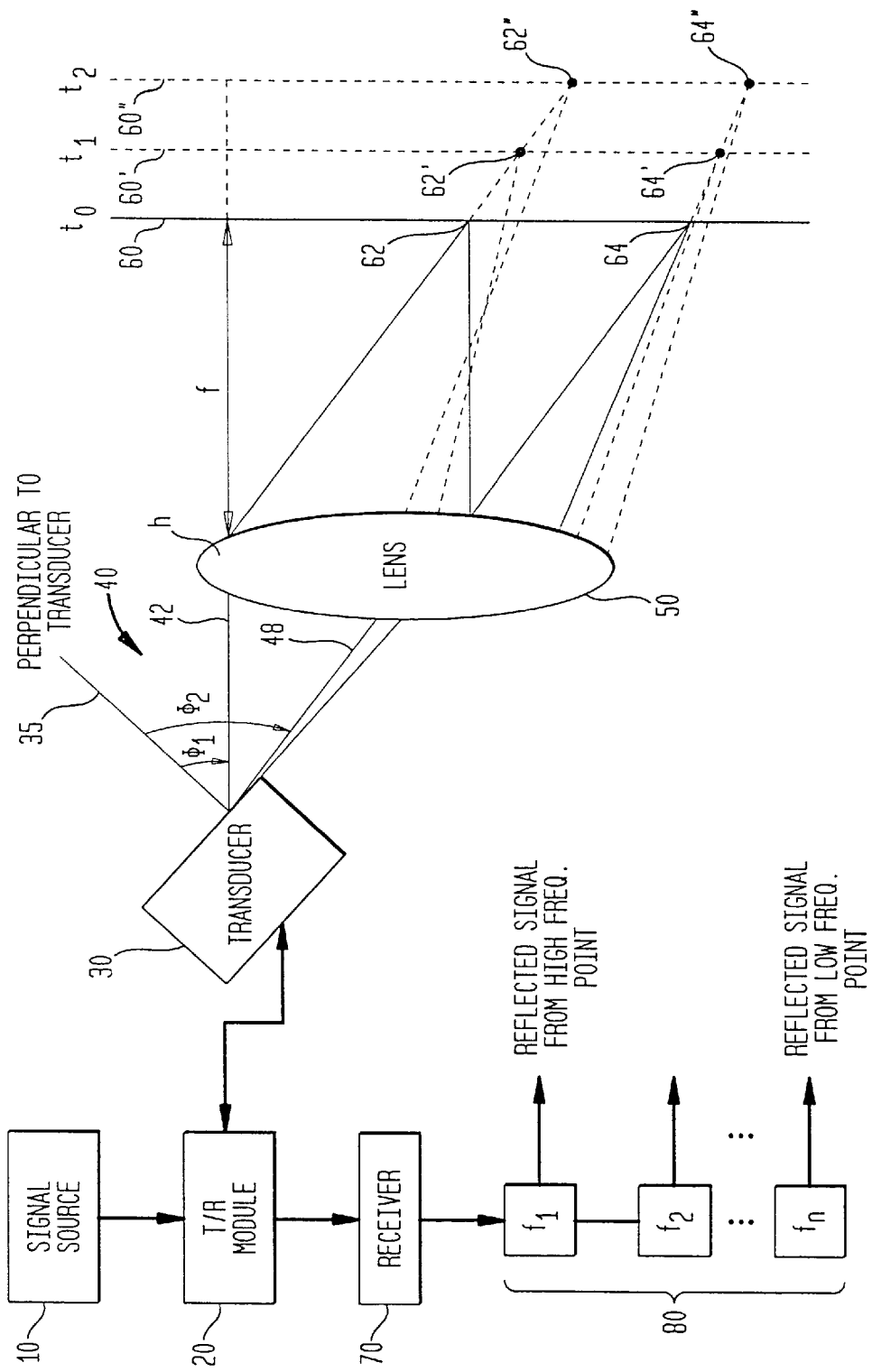
FIG. 1B is a diagram of the imaging system apparatus showing the temporal penetration of signal frequencies to obtain multi-dimensional visualization of an object.

To review the operation, as shown in FIG. 1A, a series of frequencies applied to the transducer 30 produces a series of angled beams 40, each of a different frequency; each frequency-beam will focus to a different point on focal plane 60 after passing through lens 50. Note that one beam corresponds to one frequency, and that one frequency corresponds to one point or spatial position. Depending upon the reflectivity of that area, a certain portion of the impinging energy will be reflected, pass back through lens 50, and impact the transducer at the angle appropriate for that frequency. The amount of reflected energy at that frequency shows the reflectivity of the corresponding point. As a number of frequencies are used simultaneously, and the reflected energy in the frequencies measured simultaneously using the filter bank 80 of reflecting signal filters, a series of points can be measured simultaneously. This is particularly important for 3-D visualization. By rotating the grating-lens combination, a series of lines of points, like spokes is produced. As one can ascertain, an area is covered by varying the positions of the spokes. By repeating this process and sampling at a number of depths corresponding to time intervals associated with the speed at which the pulse travels, a volume of data is generated for 3D visualization. FIG. 1B illustrates a sampling at depths $t_0$, $t_1$, $t_2$ (corresponding to spatial positions 60, 60', 60'') for generating data for 3D visualization.

Figure 3:
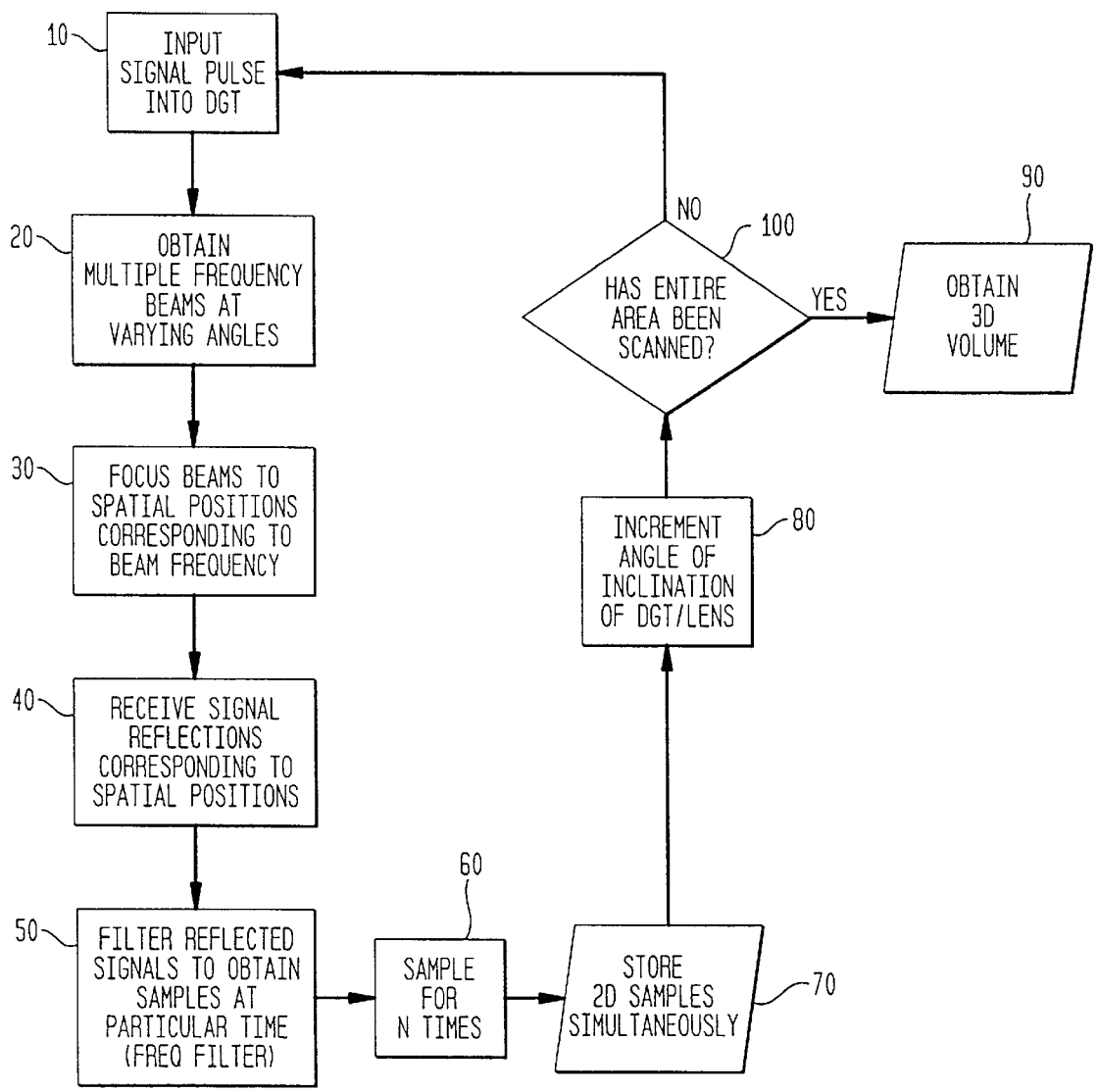
FIG. 3 is a schematic depicting the steps in obtaining a three dimensional visualization of an object according to the present invention.
Figure 6:
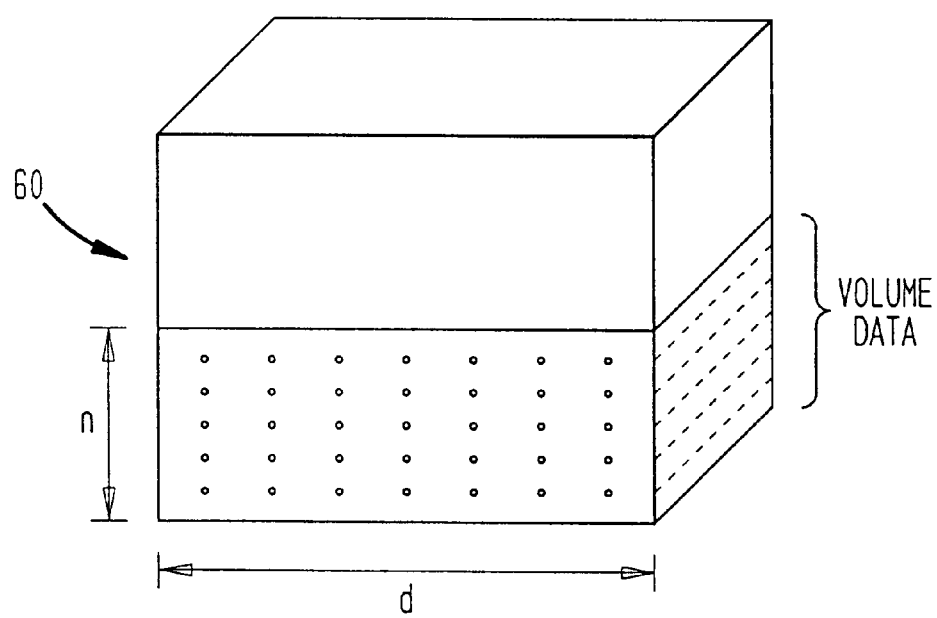
FIG. 6 is a pictorial representation of the stored image data samples according to the present invention.

Referring now to FIG. 3 there is shown a method of pulse echo imaging using simultaneous multiple beams. A short duration signal pulse is transmitted into the quadrature diffraction grating transducer (module 10) resulting in multiple frequency beams at varying angles with respect to a perpendicular from the diffraction grating transducer (module 20). The beams are then focused (module 30) to generate intensity spots at spatial positions corresponding to beam frequency. Signal reflections which correspond to the reflectivity of those spatial positions are then received in module 40 and are filtered to obtain samples corresponding to the reflectivity of those spatial positions and hence frequencies at a particular time (module 50). These signal reflections are sampled, stored (module 60) and filtered to represent the back scattered signal data as the signal progresses in time or depth ($t_0$, $t_1$, $t_2$ as shown in FIG. 1B). Such samples are obtained at predetermined intervals corresponding to the pulse width of the input pulse. As shown in FIG. 6, n lines corresponding to the number of filters (of points) of depth d (i.e. "time divided by the pulse width") are stored in a memory unit 60 such as a microprocessor RAM. The diffraction grating transducer lens combination is then rotated (module 80) and the process repeated such that a volume of data is generated for 3D visualization (module 90) upon completion of rotation around the entire circumference of the object.

As shown in FIG. 1A, the DGT 30 is angled to the desired field-of-view so that the highest frequency 42 (lowest angle) beam goes parallel to the axis, and the lowest frequency 48 beam goes as shown. For simplicity, the lens 30 is shown as separated from the DGT 30, but for maximum efficiency, the grating would be constructed as part of the lens structure, i.e., as one solid unit. For example, if a single sinusoid of frequency f.0, as shown in FIG. 2, is applied to a broad-bandwidth QDGT, the resulting frequency spectrum would consist of a range of frequencies over the range of 2 f to zero in a sinc form, as shown.

$$I_n = \frac{\sin[\Pi \cdot \{(f_0 - f_n)/f_0\}]}{\Pi \cdot \{(f_0 - f_n)/f_0\}}$$

where $I_n$ is the intensity.

Figure 2:
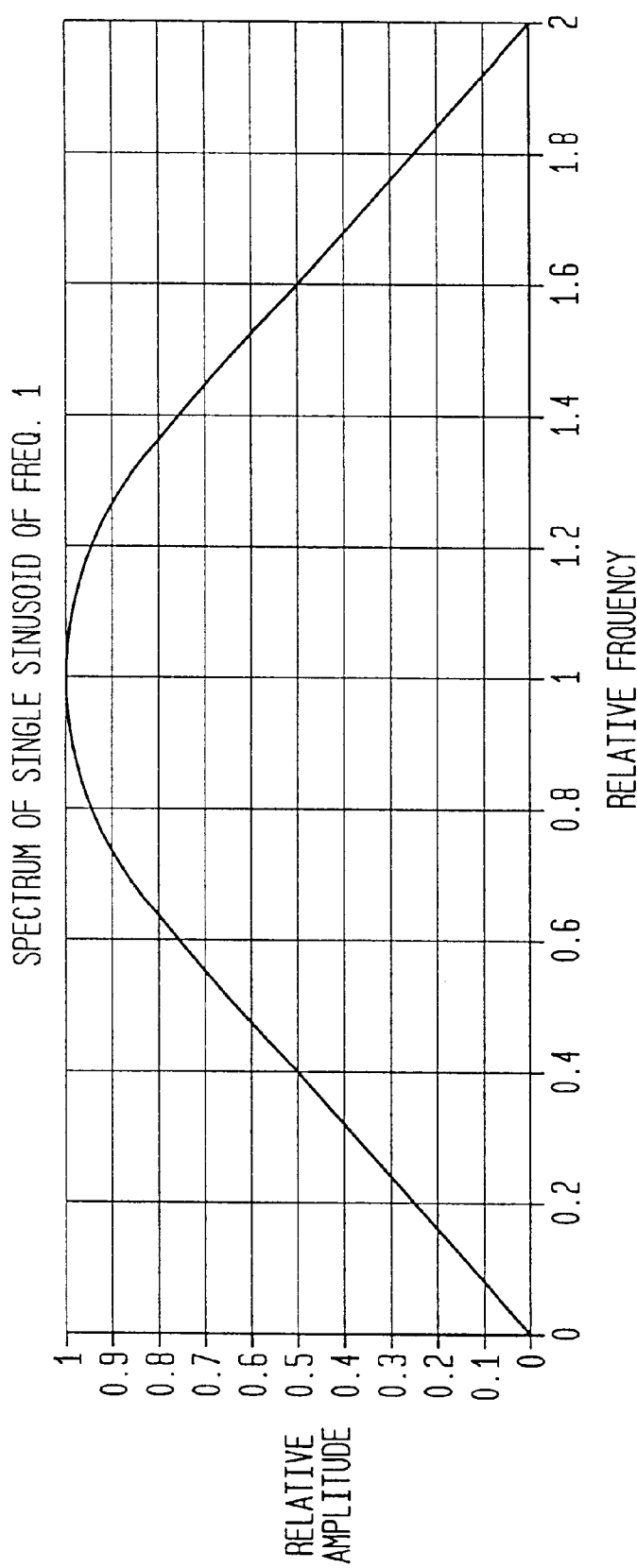
FIG. 2 is an exemplary diagram of a single sinusoid pulse of given frequency as input to the transducer according to the present invention.

Assuming a DGT 30 with periodicity of 0.26 mm and a center frequency of 15 MHZ, and using the single sinusoid drive in FIG. 2, the half-amplitude frequencies of 0.4×15 and 1.6×15, or 6 MHZ and 24 MHZ, correspond to 74° angle for the low frequency and 14° angle beam for the high frequency. While a pulse consisting of multiple frequency short pulses may be generated that would allow one to direct where the energy goes, for simplicity it is assumed that the single sinusoid excitation of FIG. 2 is provided. If the DGT is angled backward at 14 degrees, the high frequency beam 42 will be parallel to the axis of the lens, and therefore focus on the focal plane at the center point. Note that one could also tilt the DGT 30 in the opposite direction, point the beam in the opposite direction, and affect the same operation, if mechanically desirable. If the focal length f of the lens is 48 mm, and the half-height h of lens 50 is 3 mm (i.e. an f/8 lens), the low frequency point defining the edge of the field will be at tan(74−14)*48 or 83 mm down from that axis. The resolution (before considering the effect of spectral bandwidth, discussed below) of the point at the center will be f$\lambda$/h=0.75 mm, and the resolution of the point at the bottom of the field will be 3* cos(74−14)$^{-1}$ or 6 mm. Use is made of the fact that the distance from the center to the first zero in amplitude of a focused spot is 1.22 f$\lambda$/a, where a is the aperture of the lens; if the center of a beam is moved by that amount, a new spot is "resolved". The angular resolution is approximated as $\lambda$/a. In addition, while the spot is constant in size in terms of sin$\theta$, in terms of the flat focal field, as the angle increases there is a factor of cos$\theta^{-1}$, as examination of the spot on an arc versus the flat focal plane will show. The resolution (due to focus) near the middle will be approximately 2 mm. To attain the same 2 mm resolution along the axis as the middle of the field, one would use a frequency bandwidth in the band of filters 80 such that the pulse duration would be about 2.5 microseconds, as the axial resolution is 0.75 mm per microsecond. This corresponds to a 400 KHz bandwidth. Therefore, from this consideration, there could be a total number of points of the total bandwidth divided by the bandwidth of the filters, or 18/0.4=45 frequency bands to examine.

The bandwidth used also affects the spatial resolution. The angle is given by the arcsine ($\lambda$/d). Thus, as $\lambda$ changes, the angle changes. Note that by simple expansion:

sin($\theta$+$\delta\theta$)=$\lambda$/d+$\delta\lambda$/d; (sin($\theta$+$\delta\theta$)=sin$\theta$ cos$\delta\theta$+cos$\theta$ sin$\delta\theta$; for small $\delta\theta$, this=sin$\theta$+cos$\theta$ $\delta\theta$; sin$\ominus$=$\lambda$/d).

Subtracting sin$\theta$=$\lambda$/d from both sides gives cos$\theta$ $\delta\theta$=$\delta\lambda$/d; or $\delta\theta$=$\delta\lambda$/(d cos$\theta$); as sin$\theta$=$\lambda$/d & tan$\theta$=sin$\theta$/cos$\theta$, $\delta\theta$/sin$\theta$=($\delta\lambda$/$\lambda$)/cos$\theta$.

Therefore $\delta\theta$=($\delta\lambda$/$\lambda$)*tan$\theta$).

Therefore the size of the spot which is imaged by a particular frequency band will be a spatial convolution of the ideal frequency with the spectral band, multiplied by tan $\theta$. For the "averaged" or representative parameters chosen in this example, this has the effect of reducing the number of resolvable points by approximately one half. That is, for the central points around 24 MHz, the 400 KHz bandwidth represents a change in angle of 0.4/24, or 0.016; the change in angle due to the finite aperture, $\lambda$/d, is 0.021. Therefore, for the points near the axis, the spectral bandwidth only moderately affects the resolution; at the high angle, low frequencies, such as 6 MHZ, where the fractional bandwidth is 0.07 and tan $\theta$ is 1.7, it will expand the spot by 0.11 while the finite aperture causes an angular uncertainty of $\lambda$/d of 0.08. Thus, it will dominate the resolution for this constant bandwidth configuration. On the average, the number of resolvable elements will be about half of what otherwise they would be. (From the aperture size, the total angle $\theta$ of about 1 radian, the angular resolution given by $\lambda$/a is 0.1/3=0.03, or ~33 resolvable spots; the combination of the spectral width effects and the finite aperture convolved would yield ~20 resolvable points.)

An alternative approach is to have the axial resolution match the lateral resolution; this would entail constant percentage bandwidth, for example, 1 MHZ for the 24 MHZ point and 166 Khz for the 6 MHz point. However, the total number of points would be similar. There are a number of tradeoffs of frequency range vs lateral and axial resolution, number of points on the focal plane, design of the lens, including its focal length and curvature, that can be adjusted by one skilled in the art.

By rotating the above described system around the axis of the lens, using a drive similar to existing side-looking ultrasound systems, a round image consisting on "spokes" resulting from each pulse from signal source 10 can be generated. If the spot size at the edge of the field, corresponding to the 6 MHz point, is ~6 mm (double the width of the spatial-only effects), there would need to be enough spokes so that the circumference, 83*2*$\pi$, divided by the spot size of 6, is continuously sampled, or 87 spokes as shown in FIG. 7. If one oversamples by 2, the number of pluses required would be 174. As the round trip for each pulse is, for a 100 mm depth of field, given by the total travel distance divided by the velocity of sound of 1.5 mm/microsecond, is approximately 166 microseconds (200/1.5), generating an image would require 174*166 microseconds, or about 29 milliseconds.

As a full 3-D volume image can be generated by multiple sampling in time while the pulses propagate through the region of focus (which for the f/8 system would be about 7$\lambda$f#$^2$ or approximately 40 mm), this indicates that approximately 1000/29, or over 30 volumes a second, each volume consisting of a cylinder about 166 mm in diameter by 40 mm deep of acoustic information could be generated. This real-time volume will have been generated by a rotating structure only 3 mm in diameter, suitable to be mounted on a catheter and, for example, placed inside the heart.

While the discussion above concerned using a lens, other equivalent methods of converting angle to position may also be used. In an alternative embodiment, a curved surface such as a reflector may be used to act like a lens. This produces focussed points for each frequency, but the focus of the points tend to be a curve. Mounting the DGT 30 on a curved surface achieves such a result. As is well-known to those skilled in the art, a curved surface can affect focussing just as a lens can. However, producing a diffraction-grating transducer on a curved surface may be more difficult and mechanically challenging than attaching a flat quadrature-driven diffraction-grating-transducer (QDGT) to a lens.

Another method of producing multiple point-like focus areas is to build in focussing into the array by changing the spacing of the elements as a function of position. By having the elements of the transducer 30 at different and decreasing spacing d1, d2, . . . , dn, such that they diffract at one angle at one end and at a higher angle at the other end, as shown in FIG. 8, the rays cross at the focus point f. The greater the curvature, the less the element spacing needs to vary. Again, a broad-band (or combination of various frequency sinusoids) excitation will produce a multiplicity of focussed points, by the principal of superposition. This design procedure has the advantage of comprising essentially a single element. However, drawbacks include additional restrictions on the possible element spacings to ensure that higher-orders do not appear in the image, in additional to posing manufacturing challenges.

The disclosed apparatus and device has the potential of being a simple to build and operate imaging system that provides high resolution (particularly at the center of its image), three-dimensional images. However, since the system uses a broad bandwidth, the penetrations through tissue will vary with position, with the center high frequencies being quickly attenuated and the image-edge low frequencies propagating well. Note that if the system is used as a sidelooker, i.e. the axis of the DGT being along the axis of the rotating wire, the high frequencies would be more perpendicularly directed out and the low frequencies usefully directed forward.

It should be noted that the production of multiple beams means that the imaging power in each beam is limited, as the available power is divided among the beams. However, this may not pose a significant problem, because the usual limitation on medical imaging power is the spatial peak power rather than the total power. In such a situation, the use of multiple points of focus allows greater overall power to be used.

Given these characteristics, and the fact that today the best 3-D volume images are volume renderings wherein the image can be "segmented", such as blood versus tissue, use of this imaging system is well suited for mapping internal organs such as the interior of the heart. The images are well represented by two volumes, blood and tissue, and the blood will not significantly differentially attenuate the different frequency beams.

An apparatus comprising a diffraction grating transducer plus focussing means, and a method, using broad-bandwidth frequency excitation of that apparatus coupled to a filter bank, has been disclosed that allows pulse-echo ultrasound medical imaging with simultaneous multiple beams. This invention should prove useful for both forward and side-looking 3-D volume medical ultrasound imaging.

While there has been shown and described the preferred embodiments of the invention, other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

What is claimed is:

1. An ultrasonic imaging apparatus comprising:
   a quadrature diffraction grating transducer (QDGT) comprising an array of transducer elements for receiving a series of pulses of energy at a predetermined pulse rate and generating a plurality of beams at different angles corresponding to a plurality of frequencies toward an object to be imaged;
   a lens coupled to said QDGT for physically separating different angle beams produced by said QDGT and focusing said beams to produce an array of focused points at spatial positions on said object;
   a receiver for receiving reflected signals from said object having frequencies corresponding to said spatial positions, said receiver comprising a plurality of frequency filters operating in parallel, each filter selectively tuned to a different frequency for simultaneously receiving and separating the frequency components of said reflected signals to produce sample image data sets corresponding to spatial positions at particular time intervals;
   means for producing rotational motion between a combination of said QDGT and said lens, and said object to enable generation of sample image data sets at other predetermined spatial positions; and
   means for summing said sample image data sets at each of said predetermined spatial positions to produce a three dimensional image of said object.

2. The apparatus according to claim 1, wherein said lens has an index of refraction less than one.

3. The apparatus according to claim 1, wherein said lens is made of plastic and has a concave surface.

4. The apparatus according to claim 1, wherein said imaging apparatus is smaller than the volume of the object to be imaged.

5. A method for producing an image using an imaging system comprising the steps of:
   transmitting a series of pulses of energy at a predetermined pulse rate through a quadrature diffraction grating transducer QDGT toward an object to be imaged to generate a plurality of beams at different angles corresponding to a plurality of frequencies;
   disposing a lens in optical alignment between said QDGT and said object for physically separating different angle beams produced by said QDGT and focusing said beams to produce an array of focused points at spatial positions on said object;
   receiving reflected signals from said object having frequencies corresponding to said spatial positions;
   simultaneously filtering said reflected signals to produce sample image data sets corresponding to spatial positions at particular time intervals;
   rotating said QDGT and said lens about said object for generating sample image data sets at other predetermined spatial positions; and
   summing said sample image data sets at each of said predetermined spatial positions for producing an image from said sample image data sets.

6. A method for producing an image using an imaging system comprising the steps of:
   providing a diffraction grating transducer formed of an array of parallel transducer elements, each having different spacing values such that diffraction at one end of said array occurs at a first angle, and diffraction at a second end of said array occurs at a second angle greater than said first angle;
   transmitting a pulse of energy through said diffraction grating transducer toward an object to be imaged to generate multiple beams at different angles corresponding to multiple frequencies;
   focusing said beams to produce an array of focused points at spatial positions on said object, each corresponding to a particular one of said multiple frequencies, and having reflected signals from said object having frequencies corresponding to said spatial positions; and
   simultaneously filtering said reflected signals at distinct frequencies to produce sample image data sets corresponding to the reflectivity of said spatial positions and frequencies at particular time intervals.

7. The method according to claim 6, further comprising the steps of:
   rotating said transducer and lens with respect to said object and summing said sampled image data sets to produce a three-dimensional image of said object.

8. The method according to claim 7, wherein said rotation is performed in angular increments of five degrees.

* * * * *